(12) United States Patent
Dhawale et al.

(10) Patent No.: US 6,314,160 B1
(45) Date of Patent: Nov. 6, 2001

(54) METHOD AND APPARATUS FOR PERFORMING FLUOROSCOPIC NOISE REDUCTION

(75) Inventors: Paritosh Jayant Dhawale, Selkirk, NY (US); Thierry Lebihen, Versailles (FR); Gregory Michael Kautz, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/465,313

(22) Filed: Dec. 17, 1999

(51) Int. Cl.$^7$ .................................................. H05G 1/64
(52) U.S. Cl. .......................................... 378/98.2; 378/98.4
(58) Field of Search ................................. 378/98.2, 98.4, 378/98.7

(56) References Cited

U.S. PATENT DOCUMENTS

| | | | |
|---|---|---|---|
| 4,367,490 | 1/1983 | Riederer | 358/167 |
| 5,091,925 | * 2/1992 | Haendle et al. | 378/98.2 |
| 5,495,514 | * 2/1996 | Forbachek et al. | 378/98.2 |

* cited by examiner

Primary Examiner—David V. Bruce
(74) Attorney, Agent, or Firm—Donald S. Ingraham; Douglas E. Stoner

(57) ABSTRACT

The present invention provides an adaptive fluoroscopic noise reduction (FNR) algorithm utilizing various data acquisition parameters to generate an estimation of the noise statistics and to predict a minimal object contrast associated with the object. The estimation of the noise statistics and the prediction of the object contrast are then utilized to adapt certain variables that are utilized by the FNR algorithm. The estimation of noise statistics and the prediction of object contrast may be adapted on a pixel-by-pixel basis by using a regional mean to obtain an adapted estimation of noise statistics and an adapted prediction of object absolute contrast. The variables of the FNR algorithm are then adapted based on the adapted noise statistics estimation and the adapted prediction of object absolute contrast.

30 Claims, 8 Drawing Sheets

METHOD AND APPARATUS FOR PERFORMING FLUOROSCOPIC NOISE REDUCTION

BACKGROUND OF THE INVENTION

The present invention relates to x-ray fluoroscopy systems and, more particularly, to a method and apparatus for performing an adaptive fluoroscopic noise reduction algorithm on image data acquired by an x-ray fluoroscopy system.

In x-ray fluoroscopy systems, a process known as fluoroscopic noise reduction (FNR) is performed on image frames acquired by a fluoroscopic x-ray detector of the x-ray fluoroscopy system. The objective of the FNR process is to filter noise out of the image data while preserving contrast information in the image data. To accomplish this, temporal filtering is performed on areas in the image where there is no motion. In areas in the image where there is motion, no filtering is performed.

FNR is typically performed by temporally averaging image frames in regions where there is no motion. Pixel-by-pixel motion detection is utilized to determine the existence or absence of motion in the image data from frame to frame. Therefore, pixel-by-pixel motion detection is one of the most critical stages in the FNR process because the accuracy of the motion detection affects the preservation of contrast of moving objects within the image, such as, for example, guidewires or stents.

Current FNR techniques rely on defining global limits for motion detection and these limits are applicable to the entire image. These limits affect the strength and extent of temporal averaging performed on the image data. One disadvantage of the current FNR techniques is that the global limits, which are defined a priori, are set for the entire image and do not take into account the non-stationary nature of image statistics in space. Furthermore, the global limits do not take into account the fact that object contrast and noise are functions of the exposure management (EM) trajectory parameters and other acquisition parameters of the x-ray fluoroscopy system.

Noise statistics vary as a function of mean photons in the detector elements of the x-ray fluoroscopic detector which, in turn, depends on background, the object being imaged and the EM trajectory being used. Also, the panel parameters of the x-ray fluoroscopy system play an important role in converting photon quantum noise into a digital signal for a given EM trajectory. It would be desirable to provide an x-ray fluoroscopy system that takes into account noise statistics, object contrast and other system parameters in performing motion detection and in determining the extent of temporal filtering to be performed on the image data.

Accordingly, a need exists for a method and apparatus for performing fluoroscopic noise reduction which utilize noise statistics, object contrast and other system parameters in determining which regions in an image are to be temporally filtered and, if so, the extent of the temporal filtering performed.

SUMMARY OF THE INVENTION

The present invention provides an adaptive fluoroscopic noise reduction (FNR) algorithm for performing fluoroscopic noise reduction on image data acquired by an x-ray fluoroscopy system. The FNR algorithm utilizes various data acquisition parameters to generate an estimation of the noise statistics associated with the fluoroscopic x-ray detector component of the x-ray fluoroscopy system. The FNR algorithm utilizes the data acquisition parameters and knowledge about an object to be used in an x-ray fluoroscopy procedure to predict the contrast associated with the object for a given acquisition condition, imaging geometry and patient size. The estimation of the noise statistics and the prediction of the object contrast are then utilized to adapt certain variables of the FNR algorithm.

The estimation of noise statistics and the prediction of object contrast are adapted on a regional basis, i.e., on a pixel-by-pixel basis. The variables of the FNR algorithm are then adapted using the adapted noise statistics and the adapted object contrast. Therefore, the variables of the FNR algorithm are capable of being adapted on a regional, or pixel-by-pixel, basis.

These and other features and advantages of the present invention will become apparent from the following description, drawings and claims.

DETAILED DESCRIPTION OF THE INVENTION

Figure 1:
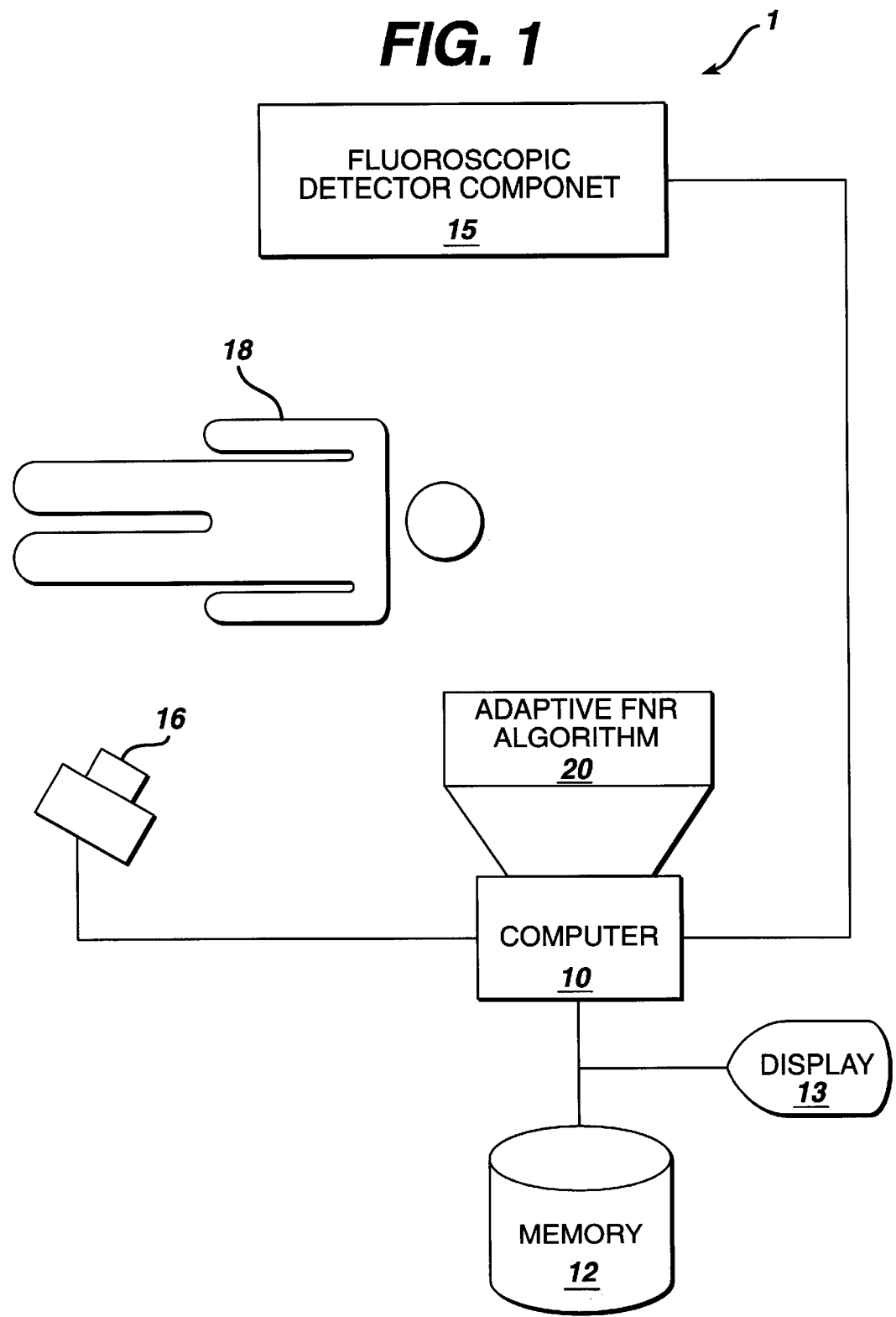
FIG. 1 is a functional block diagram of an x-ray fluoroscopy system.

FIG. 1 is a functional block diagram illustrating the x-ray fluoroscopy system 1 of the present invention that implements the adaptive FNR algorithm of the present invention. The x-ray fluoroscopy system 1 of the present invention comprises a fluoroscopic x-ray source 1, which projects x-rays onto a patient 18, and a fluoroscopic x-ray detector component 15, which detects x-rays impinging thereon and generates fluoroscopic image data. The system 1 also comprises a computer 10 that processes the fluoroscopic image data generated by the fluoroscopic x-ray detector component 15, a memory device 12 and a display monitor 13.

The adaptive FNR algorithm 20 of the present invention is not limited with respect to the type of x-ray fluoroscopy system with which the adaptive FNR algorithm 20 is utilized, as will be understood by those skilled in the art. It will also be understood by those skilled in the art that the x-ray fluoroscopy system 1 is not limited to any particular components. For example, it is well known in the art of fluoroscopy that various types of fluoroscopic x-ray detector components can be utilized for capturing x-rays and for producing fluoroscopic x-ray image data. It is also well known that various types of fluoroscopic viewing systems are available that are suitable for use with x-ray fluoroscopy systems.

Preferably, the fluoroscopic x-ray detector component 15 comprises a digital flat-panel x-ray detector. Digital flat-panel x-ray detectors are known in the art. A detector of this type that is suitable for use with the present invention utilizes a cesium iodide scintillator that absorbs x-ray photons and converts them into light. The light is converted into electronic energy by an array of photodiodes comprised in the detector. The detector comprises read-out electronics that convert the electronic charge at each pixel into digital data that is suitable for image processing by the computer 10.

However, other types of detectors are also suitable for use with the present invention. For example, an image intensifier (not shown) receives x-rays and converts the x-rays into light photons, which are then converted into electrical analog signals. These electrical analog signals may then be converted into digital signals that are suitable for processing by the computer 10.

The computer 10 is connected to the fluoroscopic x-ray source 16 and to the fluoroscopic x-ray detector component 15. The computer 10 controls the data acquisition process performed by the fluoroscopic x-ray source 16 in cooperation with the fluoroscopic x-ray detector component 15. The computer 10 may be connected to a memory device 12, which may be used for storing programs and data. The computer 10 preferably is also connected to a display monitor 13 to enable the x-ray image data that is processed in accordance with the adaptive FNR algorithm 20 to be displayed on the display monitor 13.

In accordance with one embodiment of the present invention, the adaptive FNR algorithm 20 is implemented in software, which is executed by the computer 10. However, those skilled in the art will understand that the adaptive FNR algorithm 20 may be implemented solely in hardware or in a combination of hardware and software. It should also be noted that the computer 10 is not limited to any particular type of computer. The term "computer", as that term is used herein, is intended to denote any machine capable of performing the calculations, or computations, necessary to perform the tasks of the present invention. In essence, this includes any machine that is capable of accepting a structured input and of processing the input in accordance with prescribed rules to produce an output. Therefore, those skilled in the art will understand that the computer 10 is not limited to any particular physical, structural, or electrical configuration.

Figure 2:
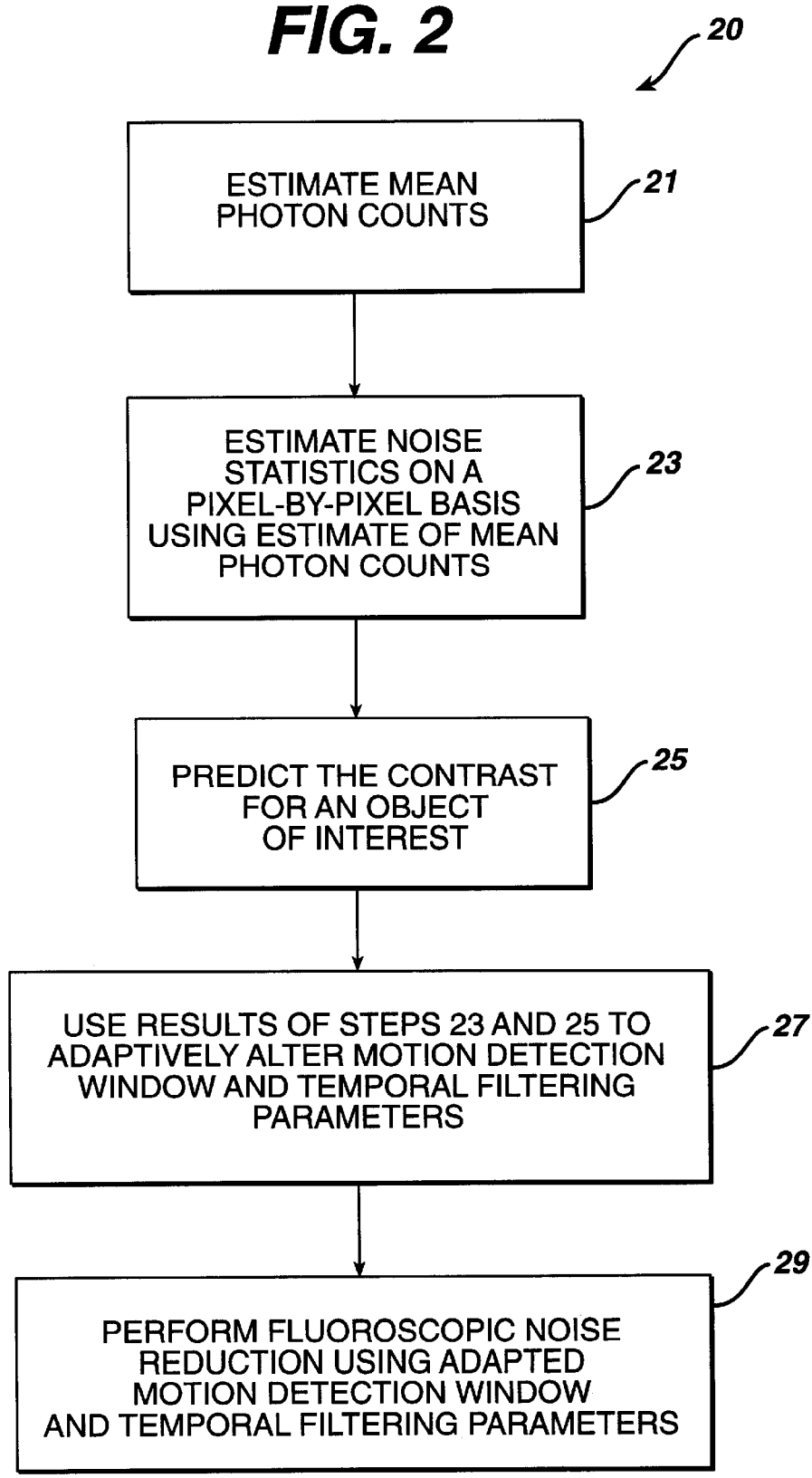
FIG. 2 is a flow chart depicting the adaptive FNR algorithm of an embodiment of the present invention.

FIG. 2 is a flow chart illustrating the functions of the adaptive FNR algorithm 20 of the present invention. As stated above, the adaptive FNR algorithm 20 of the present invention estimates noise statistics and predicts the contrast of an object of interest. The FNR algorithm 20 preferably adapts the noise estimation and contrast prediction on a regional, or pixel-by-pixel, basis. The adapted noise statistics and contrast are then utilized by the FNR algorithm 20 to adaptively define the motion detection window of the FNR algorithm 20 and to adaptively define the extent of temporal filtering to be performed on the image data. As used herein, "adaptively define" and the like refer to changing parameters that control the discrimination of the object to be imaged from the background and changing parameters with respect to the extent of temporal filtering, as described further herein. It should be noted that it is not necessary that the estimation of noise statistics and the prediction of object contrast be adapted on a regional basis. The FNR algorithm 20 will perform adequately without adapting the estimation of noise statistics and the prediction of object contrast on a regional basis. However, the FNR algorithm 20 will perform more robustly (e.g., provide improved object discrimination and noise reduction) if its parameters are adapted using a noise statistics estimation and an object contrast prediction that have been adapted on a regional basis. Therefore, the present invention will be discussed in accordance with one embodiment wherein the noise statistics estimation and the object contrast prediction are adapted on a regional basis.

In order to estimate the noise statistics associated with the input image, the mean photon count is first determined, as indicated by block 21. Fluoroscopic x-ray detector components, which are typically referred to as flat panels, have a finite gain, which is related to the conversion factor of the panel. The amount of noise is estimated from the number of electrons associated with the mean photon count, as indicated by block 23. The manner in which the noise statistics associated with the fluoroscopic x-ray detector component 15 are determined will be discussed in detail below with the respect to FIG. 3.

Once the noise statistics have been estimated, the contrast of the object of interest is predicted, as indicated by block 25. In real-time fluoroscopic imaging, objects such as stents or guidewires are manipulated in the patient's body in an area being imaged by the x-ray fluoroscopy system. The contrast of the object will depend on many factors, including the shape, size and composition of the object. The contrast of the object will also depend on other factors, including the size of the patient and the characteristics of the fluoroscopic x-ray detector component, imaging geometry and x-ray source.

By taking all of these factors into account, a model that predicts the contrast of the object in the patient's body for a given set of acquisition parameters can be generated. The model typically is based on physics and historical data. The manner in which such a model is generated will be understood by those skilled in the art. Therefore, a detailed discussion of the manner in which an object of interest, such as a stent, can be modeled will not be provided herein in the interest of brevity.

It should also be noted that the step of predicting the contrast of an object of interest commonly is implemented in the form of a look-up table (not shown). Models of various objects that are typically used in x-ray fluoroscopy are generated and the predictions regarding the contrast of the objects and these predictions are stored in a look-up table. Prior to performing an x-ray fluoroscopy procedure on a patient, the person performing the procedure inputs data into the x-ray fluoroscopy system 1 relating to the object and the size and weight of the patient. The look-up table, which may be contained in the memory device 12, for example, outputs a minimal contrast prediction associated with the information input by the person performing the procedure and the system acquisition parameters.

The contrast prediction and the noise statistics estimation are then utilized to adapt, if necessary, the FNR parameters, as indicated by block 27. The FNR algorithm 20 then performs fluoroscopic noise reduction using the adapted FNR parameters to adapt the motion detection window and the extent of temporal filtering performed, as indicated by block 29. The absolute contrast, also referred to herein as the gray level difference, associated with the object and the noise statistics estimation typically are adapted, or updated, in real time on a regional basis to thereby enable the parameters of the FNR algorithm to be adapted on a regional basis. The manner in which the gray level difference associated with the object and the noise statistics estimation are adapted on a regional basis will be discussed below with reference to FIGS. 3 and 4.

Prior to describing the FNR algorithm 20 of the present invention in detail, a discussion will be provided of the exposure management (EM) parameters and the manner in which those parameters affect the noise statistics and the object contrast. During an x-ray fluoroscopy session, x-rays are shot by the x-ray source 16 at a particular frame rate, which is typically in the range of anywhere from 5 to 30 times per second. The x-rays are shot at a given peak voltage, which is normally in kilovolts and denoted KVp. The x-ray source 1 is driven by a current, which is normally in milliamps (mA). The x-ray fluoroscopic detector component 15 has a detector dose associated with it, the characteristics of which are determined by the x-ray spectrum (i.e., the distribution of x-ray photons as a function of energy), the spectral filters, the attenuation path, the current used to drive the x-ray source 1, and the imaging geometry.

The spectral filters typically are comprised of copper, which is capable of filtering x-rays. The spectral filters (not shown) are typically located adjacent the x-ray source 16 in the path of the x-ray beam. During data acquisition, each frame is acquired by pulsing the x-ray tube (not shown) of the x-ray source 16 for a finite duration, which is commonly referred to as the pulse width of the x-ray source 16. The pulse width is typically between 1 and 20 milliseconds. The source-to-image distance (SID) and the source-to-object (SOD) determine the object magnification.

The exposure management (EM) parameters include all of these acquisition parameters, i.e., the pulse width, the frame rate, the peak voltage of the tube (KVp), the current being used to drive the x-ray source 16, the spectral filters and the detector dose. A grid (not shown) is often disposed adjacent the x-ray fluoroscopic detector component 15 in the path of the x-ray beam. This grid lessens the contrast reduction resulting from scattered photons, but also further attenuates the x-ray beam. Finite focal spot size reduces contrast, especially for small objects, and the reduction is magnification dependent. These factors are also exposure management factors that should be taken into account in determining the object contrast. Contrast is also highly dependent on the material comprising the object. Generally, materials comprised of elements which have high atomic numbers absorb x-ray photons more effectively and hence produce more contrast when compared to the background.

All of these parameters affect the contrast of the object. Some of these factors also influence the amount of noise that will be contained in the image data. Therefore, these parameters are also utilized in estimating the noise statistics and in predicting the contrast of the object in the image. The manner in which these parameters are taken into account in estimating the noise statistics and in predicting the contrast of the object will now be discussed with reference to FIGS. 3 and 4.

Figure 3:
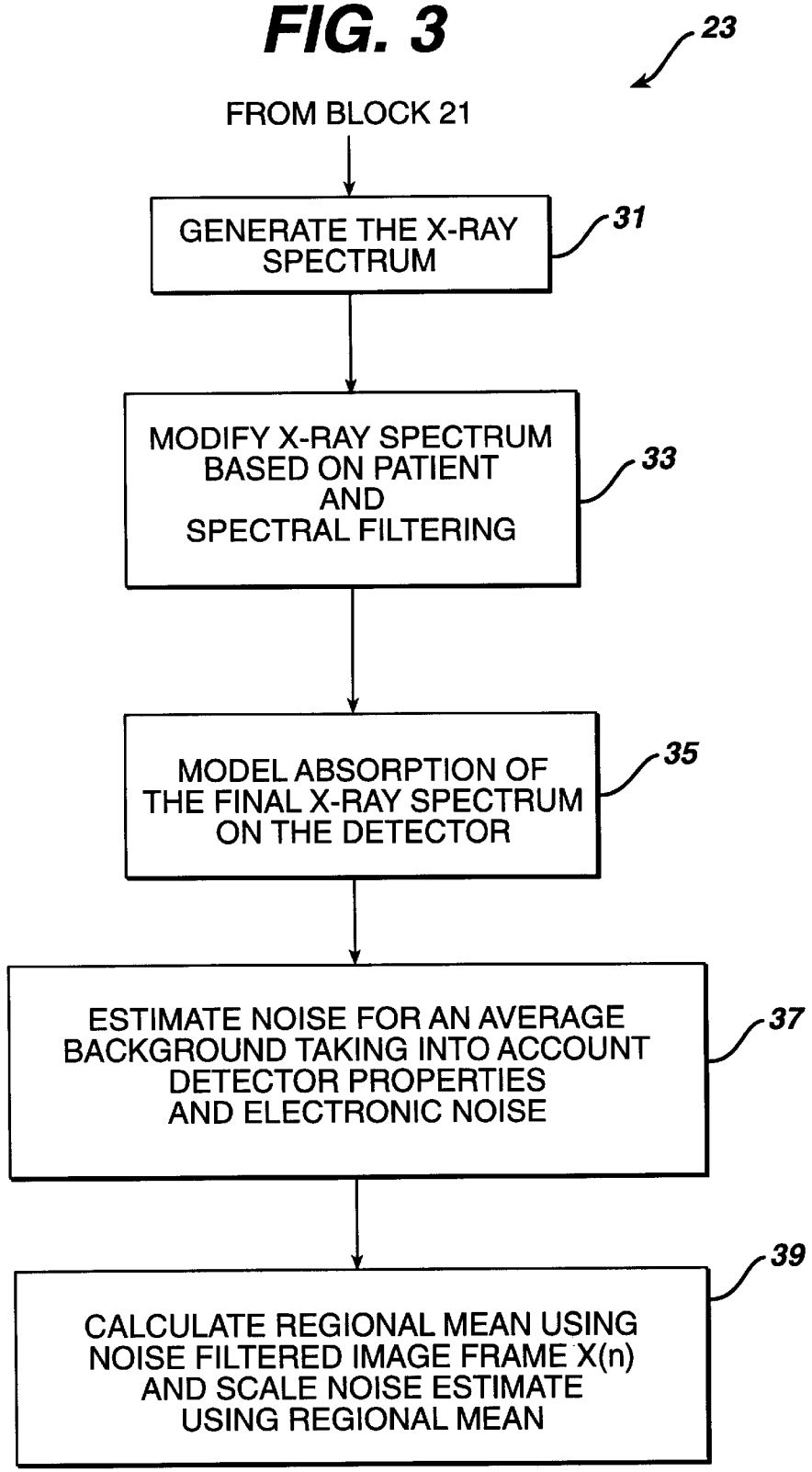
FIG. 3 is a flow chart illustrating the functions performed by the FNR algorithm depicted by the flow chart of FIG. 2 in order to estimate noise statistics in accordance with the preferred embodiment.

FIG. 3 is a flow chart functionally illustrating the steps performed in order to estimate the noise statistics. The flow chart of FIG. 3 corresponds to the step represented by block 23 in FIG. 2. As stated above, the x-ray spectrum corresponds to the distribution of the photons as a function of the energy associated with the photons, which is determined by the peak voltage (KVp), by the target material and by the target angle of the x-ray beam. Preferably, the x-ray spectrum associated with the fluoroscopic x-ray detector component 15 is calculated prior to performance of the FNR algorithm 20 and is stored in a file in memory, such as in memory device 12. For each peak voltage target angle and target material, an x-ray spectrum is stored in the file. The x-ray spectrums stored in the file preferably correspond to an x-ray source drive current of 1 milliamp (mA).

In order to obtain the x-ray spectrum associated with the detector component 15, the FNR algorithm 20 obtains the appropriate spectral file for a given peak voltage, target angle and target material from the file stored in memory. The flux is then modified to take into account inherent filtration, any spectral filters being used, as well as the filtering characteristics associated with the patient's body, as indicated by block 33. A size predictor, which is normally implemented in typical x-ray fluoroscopy systems, is utilized to predict the acrylic equivalent attenuation (that is, using acrylic material to simulate tissue) through the patient. Prior to performing this step, the flux associated with the spectral file is scaled for tube efficiency and scaled for actual current value to be utilized. The flux of the spectral file is thus modified in accordance with the inherent filtration characteristics of the tube, spectral filters and acrylic equivalent patient thickness, and the absorption of the x-ray spectrum on the detector is modeled, as indicated by block 35. Once these steps have been performed, the noise statistics are estimated for an average background taking into account properties of the detector component 15 and electronic noise contribution, as indicated by block 37.

In order to estimate the noise statistics, the number of photons per pixel corresponding to the modified x-ray spectrum is computed by pooling both scatter and primary components together. A "Swank Factor" for the resulting modified x-ray spectrum is then computed. The term "Swank Factor" is well known in the literature and results from the non-monoenergetic nature of an x-ray beam which undergoes a conversion process in a scintillator. On a sub-pixel basis, the energy deposited on the detector component 15 for the generated background is computed using the model of the absorption of the modified x-ray spectrum generated in step 35, by determining the number of photons that are associated with the absorption model and by predicting conversion of the photons into electrons.

Once the photons have been converted into electrons, the noise statistics associated with the electrons are estimated after taking into account any reduction in noise due to scintillator smoothing. Once the noise statistics have been estimated, the noise statistics are scaled using a regional mean that is calculated using an input image frame that has been noise reduced in accordance with the FNR algorithm 20 of the present invention, as indicated by block 39. The regional mean can be obtained by simply averaging a group of pixels neighboring the pixel of interest in the most recent noise-reduced image frame. Thus, the noise statistics estimation is adapted on a regional basis by scaling it using this regional mean.

It will be understood by those skilled in the art that many of the steps discussed above that are performed in estimating the noise statistics are preferable, but are not necessary to the present invention. Those skilled in the art will understand the manner in which the process discussed above for estimating noise can be varied by eliminating or modifying certain steps. The particular combination of steps discussed above with reference to FIG. 3 for estimating the noise statistics has been chosen because it optimizes the performance of the adaptive FNR algorithm of the present invention. Those skilled in the art will understand the manner in which these parameters can be utilized to estimate the noise statistics.

Figure 4:
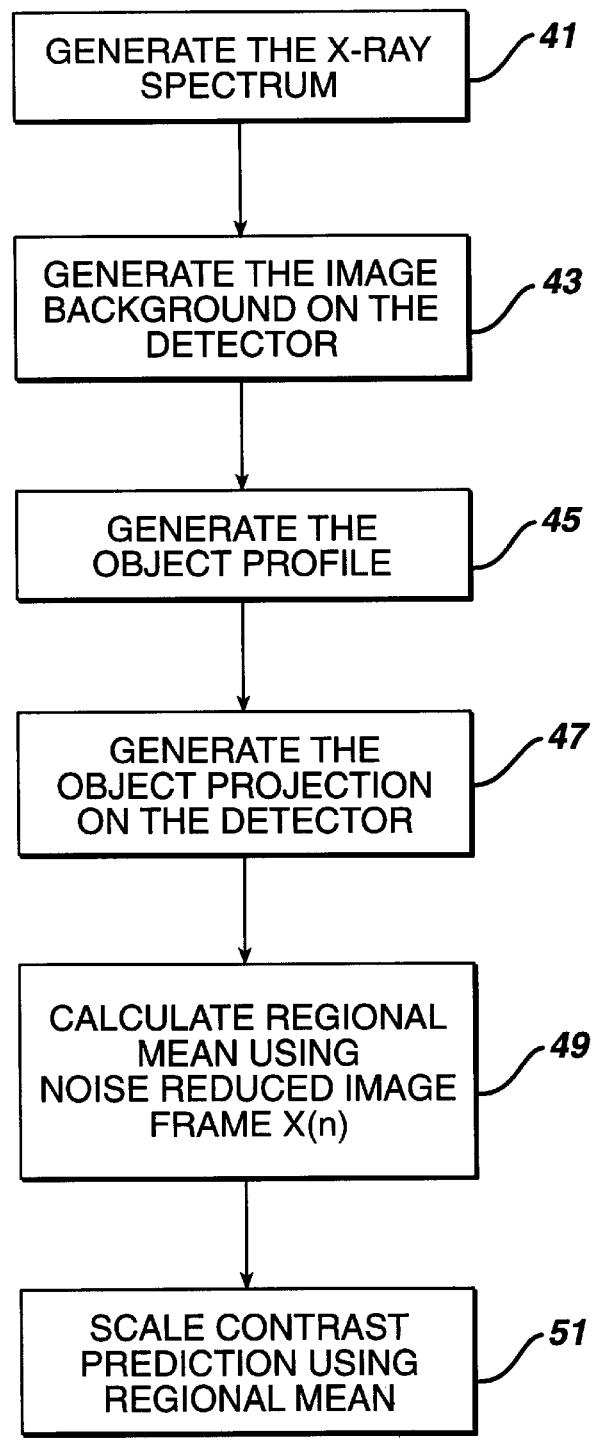
FIG. 4 is a flow chart illustrating the functions performed by the FNR algorithm depicted by the flow chalt of FIG. 2 in predicting the contrast of an object of interest in accordance with the preferred embodiment.

Once the noise statistics have been estimated, the contrast of the object of interest, which may be, for example, a stent, is predicted. However, these steps need not be performed in that order; the contrast prediction can be obtained prior to the noise statistics being estimated. FIG. 4 is a flow chart illustrating the steps performed by the adaptive FNR algorithm 20 of the present invention in predicting the contrast of the object of interest. The flow chart of FIG. 4 corresponds to the step represented by block 25 in FIG. 2. Preferably, the process of predicting the contrast of the object of interest is performed prior to the performance of a fluoroscopic x-ray procedure on a patient. Therefore, the contrast for various objects of interest preferably is pre-computed and stored in memory (e.g., in a look-up table), which may be memory device 12. A real-time scatter estimate is obtained during the procedure and is used to update the pre-computed object contrast.

It should be noted that the term "contrast" is used herein to denote a difference between the gray-level intensity of the object of interest and the intensity of the background, and by dividing the difference by the intensity of the background. In other words, if the intensity of the background is denoted by a variable A and the intensity of the object is denoted by a variable B, the contrast is defined as (A-B)/A. As stated above, the contrast, or intensity difference, is predicted, or pre-computed, and then the predicted intensity difference is updated on a regional basis, i.e., on a pixel-by-pixel basis, by estimating the regional mean. In order to distinguish between the predicted object contrast, which preferably is pre-computed, and the object contrast after it has been adapted using the regional mean, the former will be referred to herein simply as "contrast" and the latter will be referred to herein as "absolute contrast".

When a specific protocol is selected, i.e., when the x-ray parameters and the object of interest have been selected, the look-up table outputs the contrast prediction associated with the selected object. The contrast prediction is then used by the adaptive FNR algorithm 20 of the present invention during the x-ray procedure being performed on the patient. The acquisition parameters preferably are utilized to obtain the addresses in the look-up table. The manner in which the contrast prediction is used by the adaptive FNR algorithm 20 will be discussed below in detail with reference to FIG. 5.

The first step in the process of predicting the contrast of an object of interest is to generate the x-ray spectrum, as indicated by block 41. This step is essentially identical to the step represented by block 31 in FIG. 3. Once the x-ray spectrum has been generated, the image background on the detector will be generated, as indicated by block 43. In this step, the adaptive FNR algorithm 20 uses the patient size predictor discussed above to predict the acrylic equivalent attenuation through the patient. The energy deposited on the detector component 15 for the background is then computed on a sub-pixel basis by modeling the absorption of the modified x-ray spectrum in accordance with the scintillator material of the detector component 15 and the production of light photons, and by predicting the conversion of light photons into electrons. Factors such as the scatter and primary contributions associated with the imaging geometry, the patient thickness and the grid behavior are then taken into account to obtain the final image background.

Once the image background on the detector has been generated, the object profile is generated, as indicated by block 45. The shape of the object of interest and the composition of the object of interest are known. The clinical protocol to be utilized in a given procedure is also known. For example, when an interventional fluoroscopic protocol with a guidewire is selected, the object to be optimized typically is a guidewire having a diameter of 0.014 inches. On the other hand, for a diagnostic catheterization protocol, the object to be optimized is a guide catheter. Another example of a type of clinical protocol is a contrast injection procedure. In this type of procedure, the object of interest is the artery of a predetermined diameter, which is filled with contrast material.

Since the shape and characteristics of the object of interest are known, the attenuation path that will be encountered by the x-ray beam can be generated. Those skilled in the art will understand the manner in which such an attenuation path can be generated given that the shape and characteristics of the object of interest are known and the clinical protocol to be utilized and the acquisition parameters associated therewith are known. Therefore, a detailed discussion of the manner in which such an attenuation path is generated for a particular object of interest will not be provided herein in the interest of brevity.

The ratio of the source-to-image distance (SID) to the source-to-object distance (SOD) is then utilized to obtain an appropriate geometric magnification. The projection image on the object of interest is generated using the obtained geometric magnification. This is the final step in generating the object profile. Once the object profile has been generated, the object projection on the detector component 15 is generated, as indicated by block 47.

In generating the object projection on the detector component 15, the patient size predictor discussed above is utilized to predict the acrylic equivalent attenuation through the patient. The x-ray flux associated with the modified x-ray spectrum is then modified in accordance with the patient equivalent acrylic thickness. This modified x-ray flux is then utilized to generate a projection of the magnified object.

The energy deposited on the detector component 15 for the object of interest is then computed on a sub-pixel basis by modeling the absorption of the modified x-ray spectrum in correspondence with the scintillator material of the detector component 15, the number of light photons produced, and the conversion of the light photons into electrons. All of the points in the synthetic image are then replaced by the background obtained in the step represented by block 43 wherever the object of interest does not exist. The projection is then modified in accordance with the modulation transfer function (MTF) of the detector component 15, which typically is known for a given fluoroscopic detector component.

The projection is further modified by taking into account the finite focal spot blurring. The projection is then modified in accordance with the scatter and primary components resulting from modeling the imaging geometry, air gap, field of view, the patient thickness and the grid behavior. The inherent temporal lag of the fluoroscopic system 1 is then taken into account to obtain the final object projection on the detector component 15. Those skilled in the art will understand the manner in which these parameters are utilized to predict the contrast of the object of interest.

Once the contrast of the object has been predicted, it is scaled on a regional basis, pixel-by-pixel, in real-time as image frames are acquired in order to produce the gray level difference, or absolute contrast, produced by the object. Blocks 49 and 51 in FIG. 4 represent the calculation of the regional mean and the scaling of the object contrast based on the regional mean, respectively.

Many of the steps discussed above that are performed in predicting the contrast of the object of interest may be eliminated or modified, as will be understood by those skilled in the art. Many of these steps are preferred, but are not necessary to the present invention, as will be understood by those skilled in the art. The combination of the steps discussed above for predicting the object contrast is preferred because it optimizes the performance of the adaptive FNR algorithm 20 of the present invention. Those skilled in the art will understand the manner in which certain steps may be modified or eliminated altogether in order to modify the adaptive FNR algorithm 20 of the present invention. Those skilled in the art will understand that all such modifications to the adaptive FNR algorithm 20 of the present invention are within the scope of the present invention.

As stated above with respect to FIG. 2, once the noise statistics have been estimated and the contrast for the object of interest has been predicted, the estimated noise statistics and the predicted contrast are adapted on a regional basis to obtain regional estimated noise statistics and a regional absolute contrast associated with the object. The adapted noise statistics and contrast are utilized to adaptively alter the parameters of the FNR algorithm 20. Fluoroscopic noise reduction is then performed by utilizing the adapted parameters to alter, if necessary, the motion detection window and the extent of temporal filtering performed on the image. The manner in which these functions are performed will now be described with reference to FIG. 5.

Figure 5:
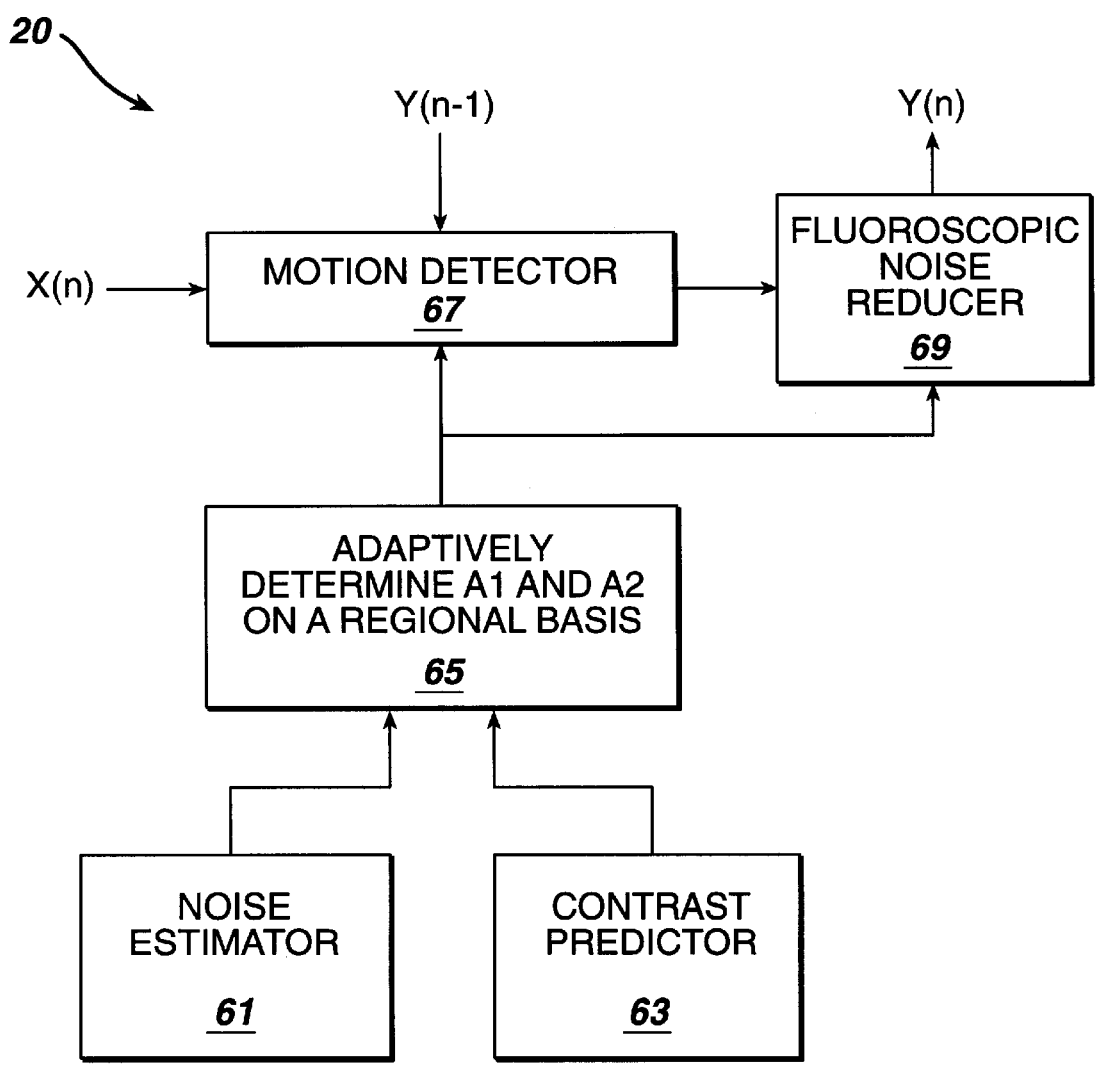
FIG. 5 is a block diagram functionally illustrating the components of the FNR algorithm of the present invention in accordance with the preferred embodiment.

FIG. 5 is a block diagram illustrating the functional components of the adaptive FNR algorithm 20 of the present invention in accordance with the preferred embodiment. Block 47 represents the motion discrimination process and block 53 represents the noise reduction process. These blocks and blocks 43, 45 and 51 will be discussed below in detail. However, prior to discussing all of these blocks in detail, a discussion will be provided of the manner in which the variables A1 and A2 shown in block 51 are obtained.

Once the adapted noise statistics and absolute contrast have been obtained, these variables are utilized to adapt the FNR algorithm 20. In accordance with the preferred embodiment of the present invention, fluoroscopic noise reduction is performed in accordance with the equation:

$$Yi(n)=f1(\Delta, \text{NOISE, CONTRAST, STRENGTH, EM})*Xi(n)+(1-f1)*f2(Yiir(n), X\_bar(n), Y\_bar(n-1), \text{EM}),  \quad \text{(Equation 1)}$$

where Yi(n) represents the output value of the current pixel i in the current frame n and Xi(n) represents the input value of the current pixel i in the current frame n. The variable Δ represents the difference between the input value of pixel i in an original, or alternatively spatially low pass filtered frame n and the same pixel output value in an original, or alternatively spatially low pass filtered output frame n−1, which corresponds to the previous frame. Therefore, the variable Δ can be expressed as X_bar i(n)−Y_bar i(n−1).

The variable EM represents the exposure management trajectory parameters and the variable STRENGTH represents the baseline strength of the filter, which preferably is selected by the user. The NOISE and CONTRAST parameters represent the adapted noise statistics estimation and the adapted object absolute contrast, respectively, obtained in the manner discussed above with reference to FIGS. 1–4. The variable Yiir(n) represents a temporally averaged response in the absence of any detection of motion. It is temporally averaged by a simple recursive equation, namely, Yiir(n)=A1*X(n)+Yiir(n−1)*(1−A1). The variable A1 will be discussed below in detail.

The function f1 is multiplied by Xi(n), which corresponds to the value of the input pixel i in frame n. This function determines the percentage of the value of the input pixel i in frame n that will be contained in the output value for the pixel i in frame n, which is represented by Yi(n). As can be seen from Equation 1, the regional noise statistics estimation and the regional contrast prediction are taken into account in determining the amount of the value of the input pixel i that will be contained in the output value of the pixel i. In other words, the regional noise estimation and the regional contrast prediction are taken into account in determining the extent of temporal filtering that will be performed on the input pixel. The exposure management (EM) parameters are also taken into account in determining the extent of temporal filtering that will be performed on the input pixel.

The function f2 generally represents some combination of past input images and past output images that have been temporally filtered, i.e., noise reduced. Therefore, the output value of pixel i for frame n retains a percentage of these past filtered values in the output value of pixel i, Yi(n).

Therefore, functions f1 and f2 operate in a manner analogous to a sliding scale such that more or all of the input value of pixel i and less or none of the temporally filtered image are contained in the output value of pixel i when motion exists. Conversely, less of the input value of pixel i and more of the temporally filtered image are contained in the output value of pixel i when no motion exists.

Equation 1 can be rewritten as follows:

$$Yi(n)=f1(\Delta, A2, \text{STRENGTH, EM})*Xi(n)+(1-f1)*f2(Yiir(n), X\_bar(n), Y\_bar(n-1), \text{EM}), \quad \text{(Equation 2)}$$

The variable A2 is obtained from the regionally-adapted noise statistics estimation and absolute contrast prediction. Therefore, the NOISE and CONTRAST prediction variables shown in Equation 1 have been replaced with the variable A2 in Equation 2. Although the variable A2 takes the EM parameters into account by virtue of the fact that A2 is dependent on the noise statistics estimation and on the object contrast prediction, EM is shown as a separate variable in Equation 2. This provides flexibility in the manner in which f1 is implemented by allowing changes in EM parameters to be factored into Equation 2 without requiring a change in the value of A2.

The variable A2 functions as a threshold value that is used to detect motion in the input image frame. The value of the variable A2 is adapted in accordance with the regionally-adapted noise statistics estimation and object absolute contrast prediction. Therefore, the value of the variable A2 is adapted on a regional basis. By adaptively altering the value of the variable A2 on a regional basis, the motion discrimination window of the FNR algorithm 20 is also adapted on a regional basis.

The value of the variable A2 is compared with the value of Δ to determine the value of the function f1. Specifically, when Δ is less than the value of A2, a determination is made by the FNR algorithm 20 that no motion exists and Equation 2 may be altered such that the function f1 is simply set equal to the value of the variable At. The function f2 is set equal to Yi(n−1), which is the output value of pixel i in the previous frame.

When Δ is less than the value of A2, the functions f1 and f2 may be stated as:

$$f1(\Delta, A2)=A1 \quad \text{(Equation 3)}$$

$$f2=Yi(n-1) \quad \text{(Equation 4)}$$

Therefore, Equation 1 can be restated as:

$$Yi(n)=A1*Xi(n)+(1-A1)*Yi(-n1) \quad \text{(Equation 5)}$$

When Δ is greater than the value of A2, the function f1 is set equal to 1 and the value of the output pixel is simply assigned the value of the input pixel and no temporal filtering is performed. It will be noted that the function f2 as stated in Equations 1 and 2 is a much more generalized expression of this function than the expression given for this function in Equation 4. The function f2 as stated in Equations 1 and 2 allows the type of past image data retained in the output of the FNR process to be greatly varied, which enhances the ability to optimize the FNR process.

The value of the variable A1 preferably is varied in accordance with the difference between Δ and the value of the variable A2. When Δ is much less than the value of the variable A2, the input pixel is clearly outside of the motion discrimination window. Therefore, in this case, the extent of temporal filtering performed on the input pixel will be relatively large. Conversely, when Δ is only slightly less than the value of the variable A2, this difference indicates a boundary in the image between a region of motion and a region of non-motion. In this region, the extent of temporal filtering performed on the input pixel will be relatively small.

Therefore, the thresholding mechanism utilized by the FNR algorithm 20 to perform motion discrimination is non-linear in that the magnitude of the difference between Δ and the value of the variable A2 determines the extent of temporal filtering to be performed when Δ is less than the value of the variable A2. However, not only is the thresholding mechanism non-linear, it is adaptable on a regional basis, which results in the motion discrimination window and the extent of temporal filtering performed also being adaptable on a regional basis. This overall adaptability of the FNR algorithm 20 allows fluoroscopic noise reduction to be optimized and to be dynamically adapted on a pixel-by-pixel and frame-to-frame basis. Those skilled in the art will understand the advantages of providing an FNR algorithm that is capable of being adapted in this manner.

As stated above, FIG. 5 is a block diagram illustrating the functional components of the adaptive FNR algorithm 20 of the present invention. Block 67 represents the motion detection process during which the FNR algorithm 20 determines whether or not the input pixel corresponds to motion in the image frame. Block 69 represents the noise reduction process performed when a determination is made that the input pixel corresponds to no motion. Blocks 61 and 63 represent, respectively, the processes of estimating the noise statistics on a regional basis and of predicting the absolute contrast for the object of interest on a regional basis. Block 65 represents the utilization of the adapted estimation of noise statistics and the adapted absolute contrast to adapt the parameters A1 and A2 accordingly.

The arrows directed from to 65 from blocks 61 and 63 indicate that parameter A1 is used during the noise reduction process and that the parameter A2 is used during the motion discrimination process, as described above with reference to the equations. The parameter A2 is used to adapt the parameter A1, which is then utilized to perform noise reduction in the manner described above with reference to Equation 5.

Mathematical modeling of the system may be applied as a means to prescribe settings for the adapted parameters. As EM parameters or patient characteristics vary, other system variables are modified from their normal operating values via consideration of a system model in order to maintain similar quality in the x-ray imaging process.

For example, a change in the frame acquisition rate, an EM parameter might be desirable for compliance of regulatory dose limitations. A differing frame rate affects the perceived image quality. The FNR algorithm of the present invention can be adapted to include a temporal adaptive feature to account for changing temporal characteristics of the process (as used herein, "adapted to" and the like refer to programming or embedding an algorithm in a computer or chip to process data in accordance with a desired use of the algorithm). Through consideration of a temporal model of the complete system, a means of modifying the FNR parameters can be derived in order to provide the same imaging performance within the "system." The "system" is said to consist of the x-ray source, object/background, x-ray detector, processing, monitor, and the human observer. For illustrative purpose, a simple model of the system is imposed. For systems that include low-lag detector panels and short duration x-ray pulses to yield negligible induced smearing from object motion, the main contributors to the system temporal frequency response are as follows:

Frame acquisition/display: Assuming instantaneous image sampling and persistent display at the frame rate, $F_R$, the frequency response is:

$$H_{fps}(f) = \sin(\pi f/F_R)/(\pi f/F_R).$$

FNR Processing: Recursive FNR based upon the simplified model in Equation 5 is used, where the value of A1 is allowed to vary in response to a changing frame rate. Restating, the filter output of pixel n as $Y_n = A_1 X_n + (1-A_1) Y_{n-1}$, the filter transfer function is computed as $H_{FNR}(f) = A_1/(1-[1-A_1]e^{j2\pi f})$.

Human Observer: The observer is modeled by ideal integration over the period $T_{int}=0.1$ seconds:

$$H_{eye}(f) = \sin(\pi f T_{int})/(\pi f T_{int}).$$

Figure 6:
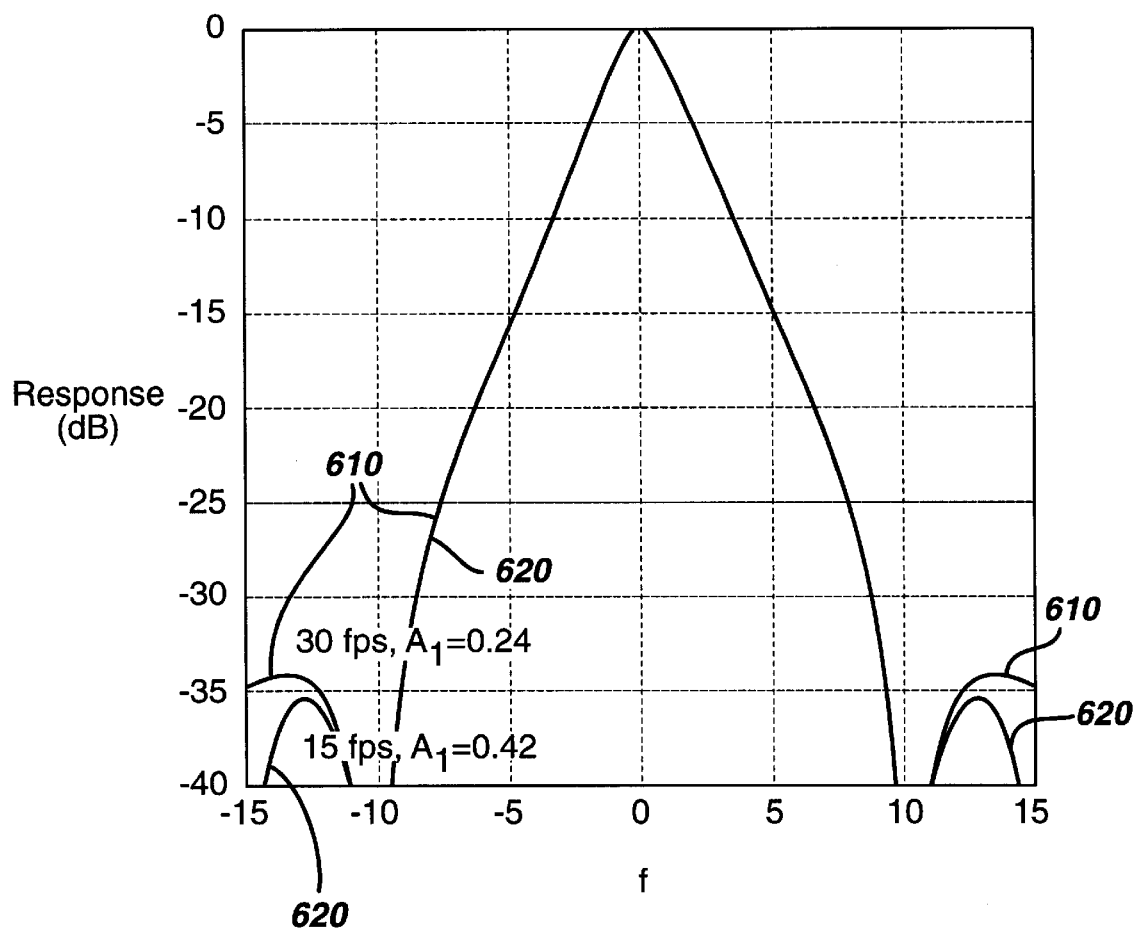
FIG. 6 is a graphic representation of matching of system responses for a temporal sampling rates of 30 frames per second (fps) and 15 fps.
Figure 7:
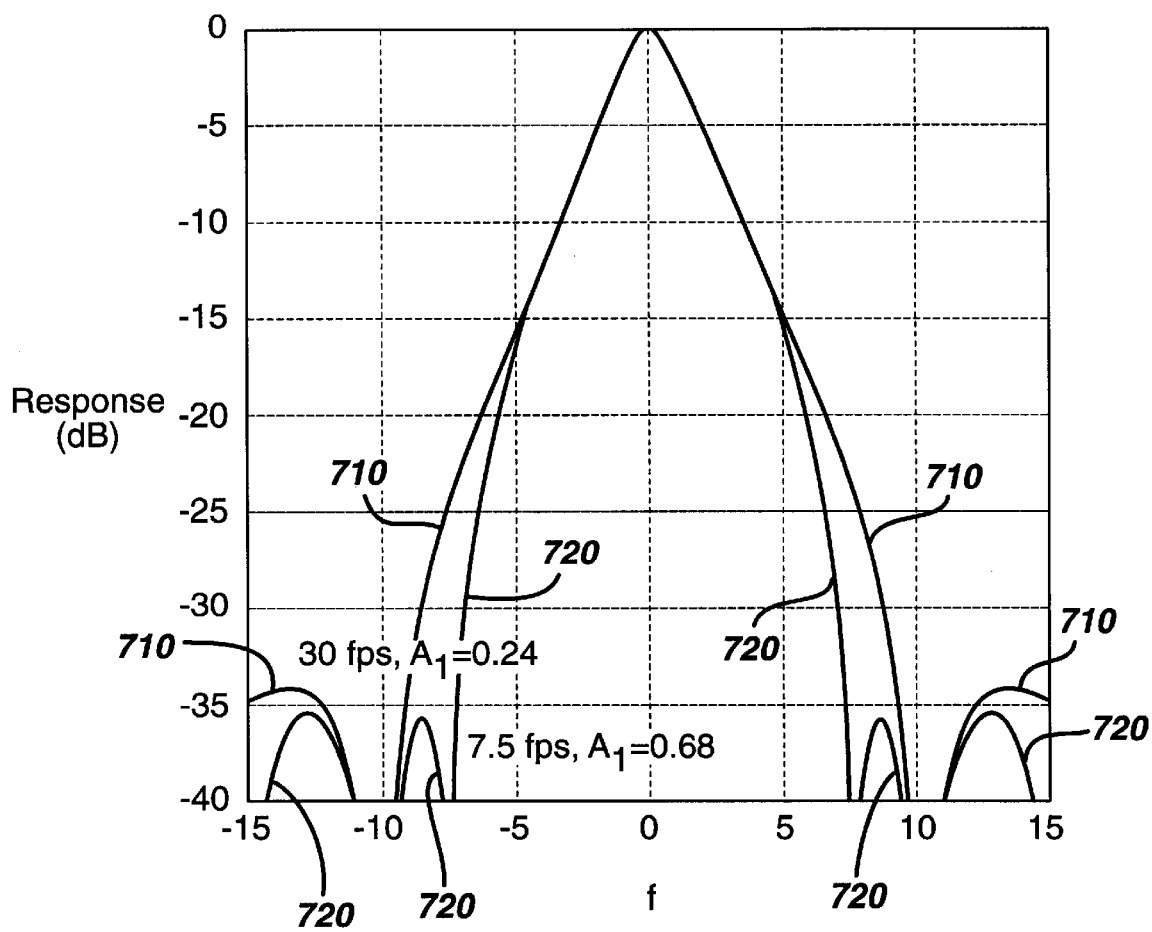
FIG. 7 is a graphic representation of matching of system responses for a temporal sampling rates of 30 frames per second (fps) and 7.5 fps.

As a result, the system is represented in the temporal frequency domain by three dominant (linear) components as $H_{system}(f) = H_{fps}(f) H_{FNR}(f) H_{eye}(f)$. Synthesis of $A_1$ is accomplished by matching (e.g., in least squares sense, visual, etc.) the spectrum to that of the reference case. As an example, consider a reference scenario of 30 fps operation with FNR value $A_1 = 0.24$. Two examples of $A_1$-synthesis (visual matching) are presented in FIGS. 6 and 7. FIG. 6 presents response data (dB) from the model for a 30 fps sampling rate in curve 610; corresponding model data for 15 fps sampling rate is shown curve 620 for the respective values of f1. Similarly, in FIG. 7, modeling data are presented in curve 710 for a 30 fps sampling rate and in curve 720 for a 7.5 fps sampling rate for the values indicated. Iterated values of A1=0.42 and 0.66, respectively in FIGS. 6 and 7, were used to visually match the two systems wherein most of the information resides (energy content mainly 7 Hz and below).

Figure 8:
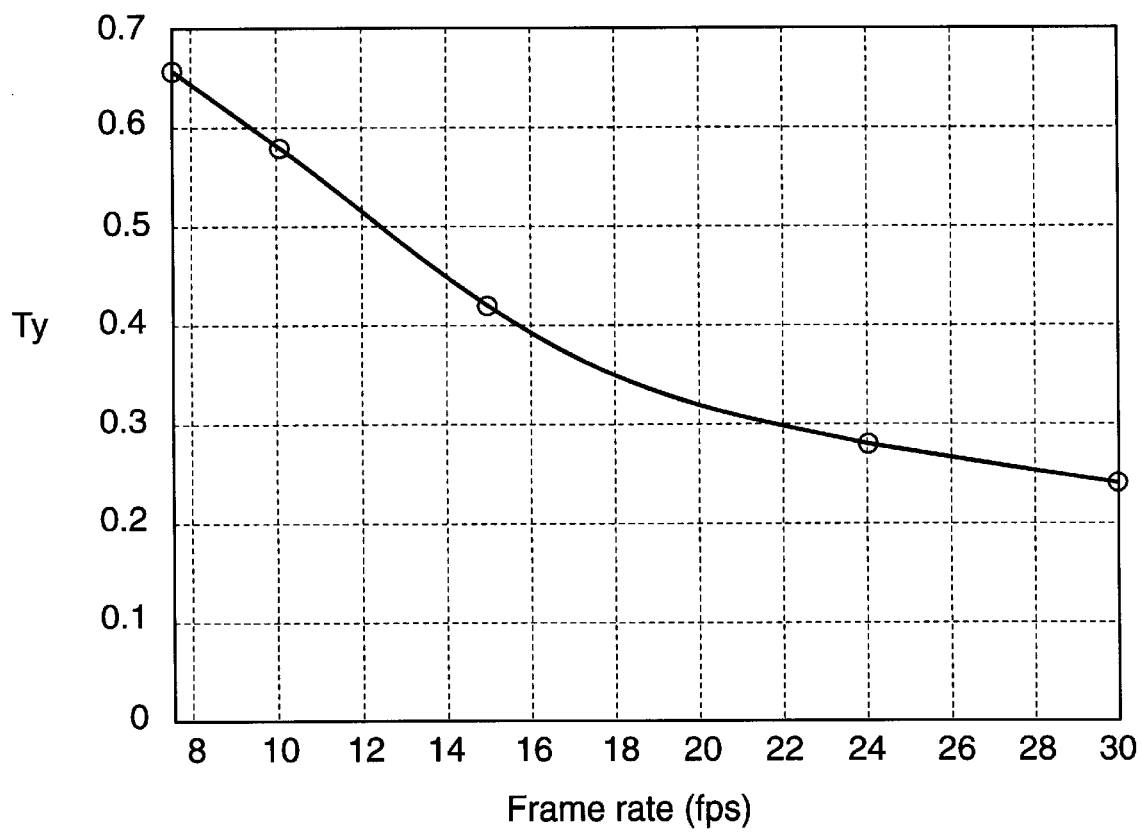
FIG. 8 is a graphic depiction of predicted weighting values for use in Fluoroscopic Noise Reduction correction system in accordance with this invention for a variety of sampling rates.

Repeating the above approach for different frame rates and collecting the optimized A1 values, the curve shown in FIG. 8 was generated. The curve prescribes the A1 setting for arbitrary frame rate to yield constant imaging performance relative to the 30 fps, A1=0.24 standard. In general, as frame rate decreases, $A_1$ is increased.

It should be noted that the present invention has been described with reference to particular embodiments, but that the present invention is not limited to these particular embodiments. Those skilled in the art will understand that many variations and modifications may be made to the embodiments discussed above and that all such variations and modifications are within the scope of the present invention. For example, those skilled in the art will understand that the functions f1 and f2 discussed above may be implemented in a variety of manners. Those skilled in the art will also understand that the parameters or variables that have been discussed above with reference to the equations are not necessarily required.

For example, although the function f2 has been illustrated as being dependent upon various present and past filtered image frames, this is intended to demonstrate the preferred dependencies of f2 and not to demonstrate the only possible dependencies for the function f2. The past and present filtered image data preferably are used to generate f2 because these image frames have already been noise reduced. The function f2 could simply be based on the filtered output pixel, Yi(n−1), for the previous frame. Those skilled in the art will understand that many such variations to the equations above may be made without deviating from the spirit and scope of the present invention.

Therefore, the functions f1 and f2, and the variable A2, are not limited to any particular functions but generally will be defined by various general rules that optimize the FNR process. For example, the following rules will apply to the behavior of the function f1. As the gray-level intensity of a region decreases, the function f1 decreases from the baseline value, which is a function of regional statistics. As strength increases, the function f1 decreases. As tile power of the x-ray tube approaches its limit, f1 decreases from the baseline value. As $\Delta$ increases, f1 increases and approaches 1 for values that are greater than or equal to A2. As pulse width increases, f1 increases. As noise increases, f1 decreases. As the regulatory limit on patient dose is approached, f1 decreases.

With respect to the function f2, this function preferably is defined as a linear combination of its variables, although this does not have to be the case. Generally, as the power of the x-ray tube approaches its limit, the strength of the spatial and temporal filters utilized by the FNR algorithm 20 to perform low pass filtering increases. With respect to the variable A2, as intensity decreases, A2 decreases from the baseline value. As strength increases, A2 increases. As the power of the x-ray tube approaches its limit, A2 increases from the baseline value. As pulse width increases, A2 remains the same or decreases. As contrast decreases, A2 decreases. As contrast increases, A2 increases.

Those skilled in the art will understand that many functions may be implemented that are suitable for dynamically adapting, the FNR algorithm 20 of the present invention in a manner which is generally consistent with these rules. Those skilled in the art will understand that other modifications and variations may be made to the present invention which are within the scope of the present invention.

What is claimed is:

1. An apparatus for performing fluoroscopic noise reduction on image data acquired by an x-ray fluoroscopy system, the system comprising a fluoroscopic x-ray source and a fluoroscopic x-ray detector component, the detector component being located to receive x-rays emitted by the x-ray source, the x-ray source emitting x-rays at a particular frame rate when driven, the detector component generating and outputting image frames of pixels in response to x-rays impinging on the detector component, each pixel having a pixel value, the apparatus comprising:

a computer in communication with the detector component, the computer receiving the image frames of pixels from the detector component, the computer being programmed to execute an adaptive fluoroscopic noise reduction (FNR) algorithm, wherein when the computer executes the adaptive FNR algorithm, the computer processes the pixel values of each image frame in accordance with the adaptive FNR algorithm to thereby perform noise reduction on the image frames, the noise reduction being performed by temporally low-pass filtering the pixel values that correspond to areas in the image frame where no motion exists, wherein pixel values corresponding to areas in the image frame where motion does exist are not filtered, the adaptive FNR algorithm estimating noise statistics and predicting object contrast and adapting at least one variable of the adaptive FNR algorithm in accordance with the estimation of noise statistics and the prediction of object contrast.

2. The apparatus of claim 1, wherein the noise statistics estimation and object contrast prediction are adapted on a pixel-by-pixel basis to obtain an adapted noise statistics estimation and an adapted object absolute contrast and wherein said one or more variables of the adaptive FNR algorithm are adapted in accordance with the adapted estimation of noise statistics and the adapted prediction of object absolute contrast.

3. The apparatus of claim 2, wherein the data acquisition parameters include exposure management (EM) trajectory parameters.

4. The apparatus of claim 1, further comprising:

a display device in communication with the computer, the computer causing the noise reduced image to be displayed on the display device.

5. The apparatus of claim 4, wherein the adaptive FNR algorithm estimates the noise statistics and predicts the object contrast by utilizing data acquisition parameters associated with the emission of x-rays by the x-ray source and the conversion of x-rays impinging on the fluoroscopic x-ray detector component into electrical signals, the electrical signals corresponding to the pixel values.

6. The apparatus of claim 4, wherein the variables utilized by the adaptive FNR algorithm include a filtering variable, A1, and a threshold variable, A2, the filtering variable A1 being utilized by the adaptive FNR algorithm to control an extent of temporal filtering performed on the pixel values in regions in the image frame where no motion exists, the variable A2 being utilized by the adaptive FNR algorithm to discriminate between regions in the image frame where no motion exists and regions in the image where motion exists, the value of the variable A2 being dependent on the adapted noise statistics estimation and on the adapted object absolute contrast prediction, the value of each pixel of a current frame being compared to the value of the same pixel in the previous image frame to obtain a difference value, $\Delta$, the value of $\Delta$ being compared to the value of the threshold variable A2 to determine whether or not the pixel in the current image frame corresponds to motion in the current image frame, wherein as the value of $\Delta$ decreases with respect to the value of the variable A2, the value of the variable A1 is adjusted to increase the extent of temporal filtering performed, and wherein as the value of $\Delta$ approaches the value of the variable A2, the value of the variable A1 is adjusted to decrease the extent of temporal filtering performed.

7. The apparatus of claim 6 wherein said adaptive FNR algorithm further comprises a temporal adaptive feature to correct for changing temporal characteristics of the acquisition of said pixel values.

8. The apparatus of claim 7 wherein the temporal adaptive feature comprises respective transfer functions for modeling frame acquisition and display, FNR processing, and human observer detection.

9. The apparatus of claim 8 wherein the temporal adaptive feature acts to increase A1 as frame rate for data acquisition decreases.

10. An x-ray fluoroscopy system, the system comprising:
   a fluoroscopic x-ray source, the x-ray source emitting x-rays at a particular frame rate when driven;
   a fluoroscopic x-ray detector component, the detector component being located to receive x-rays emitted by the x-ray source, the detector component generating and outputting image frames of pixels in response to x-rays impinging on the detector component, each pixel having a pixel value; and
   a computer in communication with the detector component, the computer receiving the image frames of pixels from the detector component, the computer being programmed to execute an adaptive fluoroscopic noise reduction (FNR) algorithm, wherein when the computer executes the adaptive FNR algorithm, the computer processes the pixel values of each image frame in accordance with the adaptive FNR algorithm to thereby perform noise reduction on the image frames, the noise reduction being performed by temporally low-pass filtering the pixel values that correspond to areas in the image frame where no motion exists, wherein pixel values corresponding to areas in the image frame where motion does exist are not filtered, the adaptive FNR algorithm estimating noise statistics and predicting object contrast and adapting one or more variables of the adaptive FNR algorithm in accordance with the estimation of noise statistics and the prediction of object contrast.

11. The x-ray fluoroscopy system of claim 10, wherein the noise statistics estimation and object contrast prediction are adapted on a pixel-by-pixel basis to obtain an adapted noise statistics estimation and an adapted object absolute contrast prediction, and wherein said one or more variables of the adaptive FNR algorithm are adapted in accordance with the adapted estimation of noise statistics and the adapted prediction of object absolute contrast.

12. The x-ray fluoroscopy system of claim 11, further comprising:
   a display device in communication with the computer, the computer causing the noise reduced image to be displayed on the display device.

13. The x-ray fluoroscopy system of claim 11, wherein the data acquisition parameters include exposure management (EM) trajectory parameters.

14. The x-ray fluoroscopy system of claim 11, wherein the adaptive FNR algorithm estimates the noise statistics and predicts the object contrast by utilizing data acquisition parameters associated with the emission of x-rays by the x-ray source and associated with the conversion of x-rays impinging on the fluoroscopic x-ray detector component into electrical signals, the electrical signals corresponding to the pixel values.

15. The x-ray fluoroscopy system of claim 14, wherein the variables utilized by the adaptive FNR algorithm include a filtering variable, A1, and a threshold variable, A2, the filtering variable A1 being utilized by the adaptive FNR algorithm to control an extent of temporal filtering performed on the pixel values in regions in the image frame where no motion exists, the variable A2 being utilized by the adaptive FNR algorithm to discriminate between regions in the image frame where no motion exists and regions in the image where motion exists, the value of the variable A2 being dependent on the adapted noise statistics estimation and on the adapted object absolute contrast prediction, the value of each pixel of a current frame being compared to the value of the same pixel in the previous image frame to obtain a difference value, $\Delta$, the value of $\Delta$ being compared to the value of the threshold variable A2 to determine whether or not the pixel in the current image frame corresponds to motion in the current image frame, wherein as the value of $\Delta$ decreases with respect to the value of the variable A2, the value of the variable A1 is adjusted to increase the extent of temporal filtering performed, and wherein as the value of $\Delta$ approaches the value of the variable A2, the value of the variable A1 is adjusted to decrease the extent of temporal filtering performed.

16. A method for performing fluoroscopic noise reduction in an x-ray fluoroscopy system, the method comprising the steps of:
   acquiring x-rays with a fluoroscopic x-ray detector component, the x-rays being emitted by an x-ray source driven at a particular frame rate, the detector component generating and outputting image frames of pixels in response to x-rays impinging on the detector component, each pixel having a pixel value;
   utilizing data acquisition parameters to estimate noise statistics;
   utilizing the data acquisition parameters and knowledge about an object of interest to predict a minimal object contrast, the object of interest to corresponding to an object utilized in a fluoroscopic x-ray procedure; and
   performing a noise reduction process on the image frames, the noise reduction process utilizing one or more variables that have been adapted based on the estimation of noise statistics and based on the prediction of object contrast, the noise reduction process being performed by temporally low-pass filtering the pixel values that correspond to areas in the image frame where no motion exists, wherein low-pass filtering is not performed on pixel values corresponding to areas in the image frame where motion does exist.

17. The method of claim 16 wherein the noise statistics estimation and object contrast prediction are adapted on a pixel-by-pixel basis to obtain an adapted noise statistics estimation and an adapted object absolute contrast prediction, and wherein said one or more variables of the adaptive FNR algorithm are adapted in accordance with the adapted estimation of noise statistics and the adapted prediction of object absolute contrast.

18. The method of claim 17, further comprising the step of:
   displaying the noise reduced image on a the display device.

19. The method of claim 17, wherein the data acquisition parameters are parameters associated with the emission of x-rays by the x-ray source and the conversion of x-rays impinging on the fluoroscopic x-ray detector component into electrical signals, the electrical signals corresponding to the pixel values.

20. The method of claim 19, wherein the data acquisition parameters include exposure management (EM) trajectory parameters.

21. The method of claim 17, wherein the noise reduction process is performed by an adaptive fluoroscopic noise reduction (FNR) algorithm being executed by a computer in communication with the detector component, the adaptive FNR algorithm utilizing a filtering variable, A1, and a threshold variable, A2, the filtering variable A1 being utilized by the adaptive FNR algorithm to control an extent of temporal filtering performed on the pixel values in regions in the image frame where no motion exists, the variable A2 being utilized by the adaptive FNR algorithm to discriminate between regions in the image frame where no motion exists and regions in the image where motion exists, the value of the variable A2 being dependent on the adapted noise statistics estimation and on the adapted object absolute contrast prediction, the value of each pixel of a current frame being compared to the value of the same pixel in the previous image frame to obtain a difference value, Δ, the value of Δ being compared to the value of the threshold variable A2 to determine whether or not the pixel in the current image frame corresponds to motion in the current image frame, wherein as the value of Δ decreases with respect to the value of the variable A2, the value of the variable A1 is adjusted to increase the extent of temporal filtering performed, and wherein as the value of Δ approaches the value of the variable A2, the value of the variable A1 is adjusted to decrease the extent of temporal filtering performed.

22. The method of claim 21, further comprising the FNR algorithm executed by the computer further comprises an temporal adaptive feature to correct for changing temporal characteristics of the acquisition of said pixel values.

23. The method of claim 22 wherein the temporal adaptive feature comprises respective transfer functions for modeling frame acquisition and display, FNR processing, and human observer detection.

24. The method of claim 23 wherein the temporal adaptive feature acts to increase A1 as frame rate for data acquisition decreases.

25. A computer program for performing fluoroscopic noise reduction on image data acquired by an x-ray fluoroscopy system, the computer program being embodied on a computer-readable medium, the program comprising:

a first code segment, the first code segment acquiring x-rays with a fluoroscopic x-ray detector component, the x-rays being emitted by an x-ray source driven at a particular frame rate, the detector component generating and outputting image frames of pixels in response to x-rays impinging on the detector component, each pixel having a pixel value;

a second code segment, the second code segment utilizing data acquisition parameters to estimate noise statistics;

a third code segment, the third code segment utilizing the data acquisition parameters and knowledge about an object of interest to predict a contrast associated with the object of interest, the object of interest corresponding to an object utilized in a fluoroscopic x-ray procedure; and a fourth code segment, the fourth code segment performing a noise reduction process on the image frames, the noise reduction process utilizing one or more variables that have been adapted based on the estimation of noise statistics and based on the prediction of minimal object contrast, the noise reduction process being performed by temporally low-pass filtering the pixel values that correspond to areas in the image frame where no motion exists, wherein low-pass filtering is not performed on pixel values corresponding to areas in the image frame where motion does exist.

26. The computer program of claim 25, further comprising a fifth code segment, the fifth code segment adapting the estimation of noise statistics and the prediction of contrast on a pixel-by-pixel basis to obtain an adapted estimation of noise statistics and an adapted prediction of object absolute contrast, and wherein said one or more variables utilized by the fourth code segment are adapted based on the adapted estimation of noise statistics and based on the adapted prediction of object absolute contrast.

27. The computer program of claim 26, further comprising:

a sixth code segment, the sixth code segment displaying the noise reduced image on a the display device.

28. The computer program of claim 26, wherein the data acquisition parameters are parameters associated with the emission of x-rays by the x-ray source and the conversion of x-rays impinging on the fluoroscopic x-ray detector component into electrical signals, the electrical signals corresponding to the pixel values.

29. The computer program of claim 26, wherein the data acquisition parameters include exposure management (EM) trajectory parameters.

30. The computer program of claim 26, wherein the fourth code segment utilizes a filtering variable, A1, and a threshold variable, A2, the filtering variable A1 being utilized by the fourth code segment to control an extent of temporal filtering performed on the pixel values in regions in the image frame where no motion exists, the variable A2 being utilized by the fourth code segment to discriminate between regions in the image frame where no motion exists and regions in the image where motion exists, the value of the variable A2 being dependent on the adapted noise statistics estimation and on the adapted object absolute contrast prediction, the value of each pixel of a current image frame being compared to the value of the same pixel in the previous image frame to obtain a difference value, Δ, the value of Δ being compared to the value of the threshold variable A2 to determine whether or not the pixel in the current image frame corresponds to motion in the current image frame, wherein as the value of Δ decreases with respect to the value of the variable A2, the value of the variable A1 is adjusted to increase the extent of temporal filtering performed, and wherein as the value of Δ approaches the value of the variable A2, the value of the variable A1 is adjusted to decrease the extent of temporal filtering performed.

* * * * *